US012636518B2

(12) United States Patent
Agarwal et al.

(10) Patent No.: US 12,636,518 B2
(45) Date of Patent: May 26, 2026

(54) HYPERTHERMIA FOR SURFACE CANCERS

(71) Applicant: Healios Therapeutics LLC, Bend, OR (US)

(72) Inventors: Ankit Agarwal, Fremont, CA (US); David Erik Greene, Bend, OR (US)

(73) Assignee: Healios Therapeutics LLC, Bend, OR (US)

( * ) Notice: Subject to any disclaimer, the term of this patent is extended or adjusted under 35 U.S.C. 154(b) by 19 days.

(21) Appl. No.: 18/930,025

(22) Filed: Oct. 29, 2024

(65) Prior Publication Data

US 2026/0083979 A1      Mar. 26, 2026

Related U.S. Application Data

(60) Provisional application No. 63/697,343, filed on Sep. 20, 2024.

(51) Int. Cl.
 *A61N 5/06*               (2006.01)
(52) U.S. Cl.
 CPC .... *A61N 5/0625* (2013.01); *A61N 2005/0626* (2013.01); *A61N 2005/0659* (2013.01)
(58) Field of Classification Search
 CPC .......... A61N 5/0625; A61N 2005/0626; A61N 2005/0659; A61N 5/0616; A61N 5/067; A61N 5/0613; A61N 2005/0644; A61N 2005/0642; A61B 2018/00452; A61B 18/203; A61B 2018/00791; A61B 2018/00642; A61F 2007/0088; A61F 7/00; A61F 7/007
 See application file for complete search history.

(56) References Cited

U.S. PATENT DOCUMENTS 5,662,643 A * 9/1997 Kung ..................... A61B 18/22
                                                                606/8
11,464,313 B2    10/2022 Wang
                        (Continued)

FOREIGN PATENT DOCUMENTS

WO     WO 2021/227675 A1    11/2021
WO     WO 2022/261986 A1    12/2022
WO     WO 2022/261988 A1    12/2022

OTHER PUBLICATIONS

Trefna, et al., "Quality Assurance Guidelines for Superficial Hyperthermia Clinical Trials" Strahlenther Onkol. (2017) 193:351-366. DOI: 10.1007/s00066-017-1106-0, Mar. 1, 2017.
(Continued)

*Primary Examiner* — Joseph A Stoklosa
*Assistant Examiner* — Adam J Avigan

(57)                ABSTRACT

In one embodiment, a method includes positioning an infrared hyperthermia heating device at least a predetermined distance away from an area of a patient's skin treated with radiation therapy and activating the infrared hyperthermia heating device to heat the area of the patient's skin. The method further includes heating, by the infrared hyperthermia heating device, the area of the patient's skin to a predetermined temperature; maintaining, using the infrared hyperthermia heating device, the predetermined temperature for a predetermined period of time; and deactivating the infrared hyperthermia heating device after the predetermined period of time to cease heating the area of the patient's skin.

23 Claims, 3 Drawing Sheets

(56) References Cited

U.S. PATENT DOCUMENTS

| | | | | |
|---|---|---|---|---|
| D1,008,546 | S | 12/2023 | Wang | |
| 11,832,698 | B2 | 12/2023 | Wang | |
| 11,986,666 | B2 * | 5/2024 | Cockrell | A61N 5/062 |
| 2004/0064167 | A1 * | 4/2004 | Berry | A61B 18/203 |
| | | | | 607/89 |
| 2004/0243200 | A1 * | 12/2004 | Turner | A61B 18/18 |
| | | | | 607/101 |
| 2008/0279946 | A1 * | 11/2008 | Hainfeld | A61P 43/00 |
| | | | | 424/94.1 |
| 2009/0024193 | A1 * | 1/2009 | Altshuler | A61N 1/328 |
| | | | | 607/100 |
| 2017/0182335 | A1 * | 6/2017 | Altshuler | A61N 1/328 |
| 2024/0108407 | A1 * | 4/2024 | Barton | A61N 5/067 |

OTHER PUBLICATIONS

Coffee, et al., "Hyperthermic Biology and Cancer Therapies: A Hypothesis for the 'Lance Armstrong' Effect", www.jama.com, Jul. 26, 2006, Jul. 26, 2006.

Jones et al., "Randomized Trial of Hyperthermia and Radiation for Superficial Tumors," Journal of Clinical Oncology, vol. 23, No. 13, May 1, 2005.

* cited by examiner

HYPERTHERMIA FOR SURFACE CANCERS

PRIORITY CLAIM

This application claims the benefit under 35 U.S.C. § 119 of U.S. Provisional Patent Application No. 63/697,343 filed Sep. 20, 2024, which is incorporated by reference herein.

TECHNICAL FIELD

This application generally relates to hyperthermia for surface cancers.

BACKGROUND

Cancer treatment often includes radiation therapy, which involves targeting cancer cells with particles (e.g., protons or certain ions) or with high-energy electromagnetic radiation (e.g., x-rays). During radiation therapy, radiation is directed at cancer cells and destroys cancer cells (and potentially other living tissues), eliminating the ability of cancer cells to proliferate. Radiation therapy can include external radiation therapy, in which the radiation source is external to the body, and can include brachytherapy, in which the radiation source is internal to the body, for example by implanting a radiation-source device in or near a tumor. Radiation treatments are often provided in courses, in which a does of radiation is provided at specific intervals (e.g., 5 out of 7 days) for a particular duration (e.g., 10-30 minutes) over a particular time period (e.g., 1-3 weeks).

Cancers can affect a wide variety of body tissues, and can occur within the body or on the body. For instance, surface cancers occur on the surface of the skin (e.g., on the epidermis) and/or within a layer of skin (e.g., within the dermis of hypodermis).

DESCRIPTION OF EXAMPLE EMBODIMENTS

Hyperthermia involves heating tissue using a heat source. Hyperthermia has shown to be effective in improving the effectiveness of radiation treatment for cancers, for example by increasing blood flow, increasing oxygenation, and impairing DNA repair mechanisms. For instance, hyperthermia can improve outcomes in cancer reduction through radiation treatments for a given radiation dose, and/or can reduce the amount of radiation needed to achieve a therapeutic result. Hyperthermia may be employed before, during or after radiation therapy. If employed before or after radiation therapy, then the hyperthermia should be applied within a particular time period (e.g., with 4 hours) of the radiation treatment.

Current hyperthermia approaches are typically expensive, time-consuming, and invasive. For instance, specialized catheter-based heating devices, ultrasound devices, and heating lamps are used to heat cancerous tissue, but these devices can be bulky, can costs hundreds of thousands of dollars, and can involve elaborate setup and maintenance. As a result, patients who receive radiation treatment often need to leave the radiation-treatment room or facility to obtain hyperthermia treatment, which is inconvenient and inefficient for both the patient and the treatment facility. In addition, the conventional approaches are time consuming, often requiring the patient to devote an hour to hyperthermia treatment on top of the time spent receiving radiation treatment, and requiring clinician time (e.g., patient monitoring) for that period of time. These drawbacks reduce hyperthermia uptake, despite hyperthermia's benefits in improving radiation treatment for cancers. This is particularly true when radiation treatment is already highly effective: the marginal improvement in outcomes when adding hyperthermia, while deeply meaningful for those patients whose outcomes end up being improved, may not be sufficient to justify hyperthermia treatment and its associated capital and temporal costs across the patient population, both from the perspective of the healthcare provider and from the perspective of a patient who does not know what benefit hyperthermia will add to their specific outcome but is faced with the real inconveniences of conventional hyperthermia approaches.

In contrast, the techniques described herein provide efficient hyperthermia treatment for surface cancers. As explained below, the techniques described herein do not require large machinery and therefore do not require the patient or provider to leave the treatment room or treatment facility in which the patient received radiation treatment. In addition, the techniques described herein provide highly controllable, quickly obtainable hyperthermia results for treating surface cancers, improving hyperthermia uptake and corresponding treatment results for both patients and clinicians.

Figure 1:
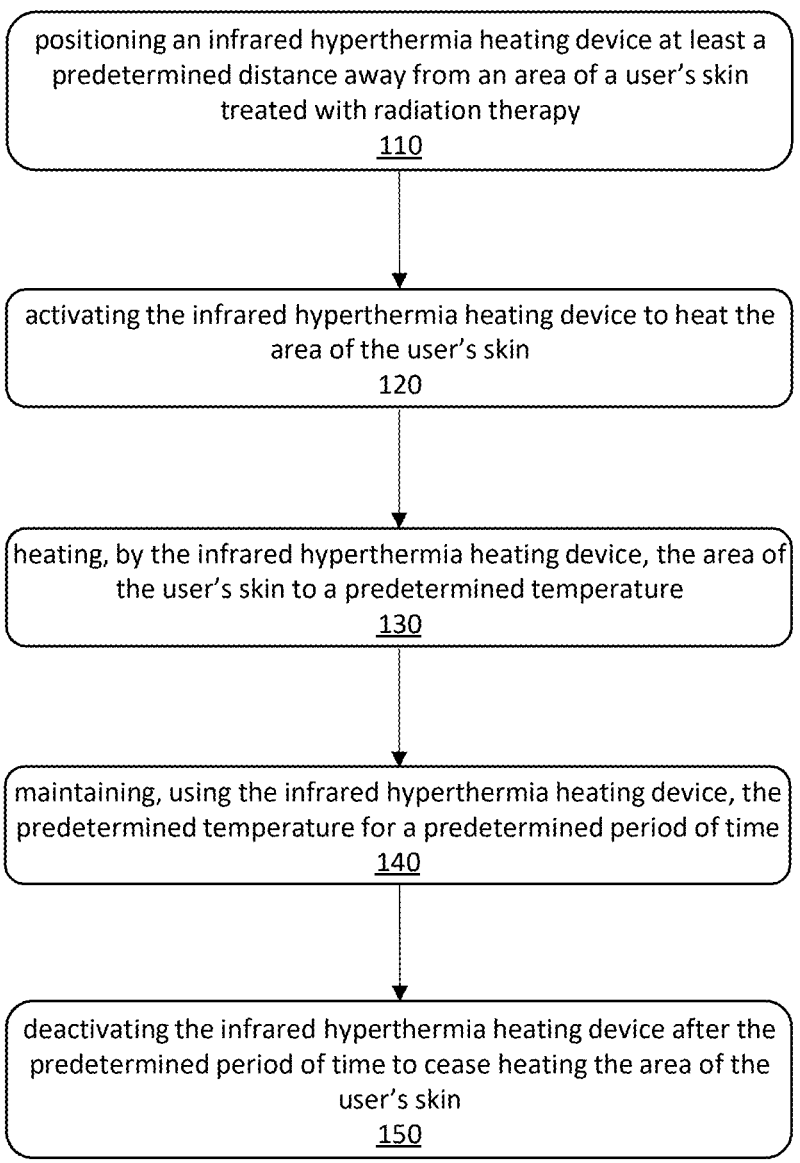
FIG. 1 illustrates an example method for efficient hyperthermia treatment in connection with radiation therapy for surface cancers.

FIG. 1 illustrates an example method for efficient hyperthermia treatment in connection with radiation therapy for surface cancers. Step 110 of the example method of FIG. 1 includes positioning an infrared hyperthermia heating device at least a predetermined distance away from an area of a patient's skin treated with radiation therapy. The radiation therapy may occur before, during, or after the application of hyperthermia. To increase effectiveness, hyperthermia should be applied less than a predetermined amount of time from a radiation treatment. For example, hyperthermia should be applied no longer than 4 hours away from a radiation treatment, but better results may be achieved if the hyperthermia is applied more coincident (e.g., within a few minutes (such as 5 minutes, or 15 minutes) before or a few minutes after) the radiation treatment.

The infrared hyperthermia heating device is external to the patient and heats the area of the patient's skin using infrared radiation emitted by the infrared hyperthermia heating device. Examples of infrared hyperthermia heating devices are described more fully below.

The infrared hyperthermia heating device should be positioned at least a predetermined distance away from an area of a patient's skin treated with radiation therapy. The area of the patient's skin treated with radiation therapy is a surface cancer, or tumor, such as squamous cell carcinoma or basal cell carcinomas, although this disclosure contemplates that any surface cancer treated with radiation therapy may benefit from hyperthermia, regardless of what tissue the cancer originates from. As used herein, a surface cancer is a cancer on or within the layers of skin, such that externally applied heat warms the cancerous tissue.

The predetermined distance ensures that the infrared hyperthermia heating device is properly positioned so as to heat, but not burn, the area of skin treated with radiation therapy. For example, in particular embodiment the predetermined distance is 3-12 inches, such as 6 inches, away from the skin, although the exact distance to be used depends on the intensity of the infrared radiation emitted by the infrared hyperthermia. As illustrated in this example, the predetermined distance in step 110 may be a distance range within which to position the infrared hyperthermia heating device. Moreover, while the above example illustrates an embodiment in which the predetermined distance is greater than 0 (i.e., the infrared hyperthermia heating device does not contact the person's skin), in other embodiments the infrared hyperthermia heating device may contact the patient's skin (e.g., as integrated into a wearable deice worn by the patient), although having some non-zero distance may help prevent burns and irritation of the patient's skin.

In step 110, positioning the infrared hyperthermia heating device includes positioning the patient or the infrared hyperthermia heating device, or both. For instance, the infrared hyperthermia heating device may be a handheld device (e.g., having handle portion 330 of the example implementation of FIG. 3) that is freely moveable by an operator. As another example, the infrared hyperthermia heating device may relatively fixed, and the patient's skin may be positioned in relation to the device.

Step 120 of the example method of FIG. 1 includes activating the infrared hyperthermia heating device to heat the area of the patient's skin. For instance, the infrared hyperthermia heating device may contain a trigger or button (each of which are examples of interface 320 of the example implementation of FIG. 3) that, when pressed, activates the infrared hyperthermia heating device. As explained here, the device's activation may be variable, for example by varying the intensity or wavelength (or both) of the infrared radiation.

Step 130 of the example method of FIG. 1 includes heating, by the infrared hyperthermia heating device, the area of the patient's skin to a predetermined temperature. For instance, the predetermined temperature may be 106° F.-110° F. As illustrated in this example, the predetermined temperature may be a temperature range within which to heat the area of skin. As explained herein, the infrared radiation controllably and relatively quickly heats the area of the person's skin to the predetermined temperature while preventing burns.

Step 140 of the example method of FIG. 1 includes maintaining, using the infrared hyperthermia heating device, the predetermined temperature for a predetermined period of time. The predetermined period of time may be between 30-90 seconds, for example around 60 seconds. In particular embodiments, the predetermined time period may start once the temperature of the area of the patient's skin reaches the predetermined temperature in step 130. After reaching this temperature, the predetermined time period may include any period of time in which the patient's skin temperature remains at or above the predetermined temperature (or the lowest temperature of a temperature range). In particular embodiments, the predetermined time period may include temperatures that exceed a predetermined temperature range. For example, if the predetermined temperature is a 106° F.-110° F., then the predetermined time period may start when the area of the patient's skin reaches at least 106° F., and may continue while that area of skin stays above 106° F., even if the temperature exceeds the upper boundary of 110° F. (although the upper boundary may influence the heating applied to the patient, as described more fully herein).

The predetermined time may be determined by fractionating a total hyperthermia treatment. For example, a patient may be prescribed 15 minutes of hyperthermia in conjunction with radiation treatment. If the radiation treatment is divided into 15 treatments, then the hyperthermia treatments will be fractioned as well (e.g., the patient will receive 15 hyperthermia treatments of one minute each).

Step 150 of the example method of FIG. 1 includes deactivating the infrared hyperthermia heating device after the predetermined period of time to cease heating the area of the patient's skin. In other words, the infrared hyperthermia heating device stops emitting infrared radiation, allowing the patient's skin to cool. After step 150, the patient's skin may be allowed to cool naturally, or with the use of cooling aids (e.g., using a cool compress). The patient may be monitored for any immediate adverse reactions, and in particular embodiment the patient may be treated with a topical lotion or gel applied to the area of skin that received hyperthermia treatment. In particular embodiments, the infrared hyperthermia heating device may be deactivated prior to step 150, for example if the patient's skin blisters or otherwise shows an excessive adverse reaction to the hyperthermia treatment.

After completing treatment, the patient's medical records may be updated to reflect that hyperthermia treatment was provided in relation to radiation therapy. For some patients, the amount of future radiation therapy may be decreased as a result of the applied hyperthermia treatment.

The infrared hyperthermia heating device emits infrared radiation, which is absorbed by human tissue, such as by surface cancers on or within the patient's skin. The absorption process generates heat, which heats the tissues that absorb the infrared radiation. Human skin absorbs infrared radiation most efficiently in the mid-infrared spectrum, particularly 3 to 10 microns. In particular embodiments, the infrared hyperthermia heating device emits infrared radiation within the mid-IR spectrum, and may specifically emit infrared radiation with a wavelength of between 6-8 microns, which overlaps with the peak absorption of water and tissue, making this range efficient for heating the skin without penetrating too deeply.

In particular embodiments, an infrared hyperthermia heating device may emit infrared radiation at a single wavelength, e.g., at a particular wavelength between 6-8 microns. In particular embodiment, the emitted wavelength may be adjustable within a range of wavelengths. By emitting infrared radiation at a single wavelength, absorption (and therefore heating) of the patient's skin is more controllable. Heating occurs as a function of wavelength and intensity (which itself depends on the emitted infrared energy, on the shape of the emitted beam, and on the distance between the device and the patient's skin), and therefore emitting infrared radiation at a relatively single wavelength controls one of the primary variables in heating a patient's skin to the predetermined temperature.

In addition, different tumors manifest at different depths relative to the patient's skin, and the depth of absorbed infrared radiation depends on the radiation's wavelength. The wavelength of the infrared hyperthermia heating device may therefore be varied based on the desired absorption depth, for example by inputting a tumor depth (or range of depths) into the device, which automatically selects a predetermined wavelength, or cycles through a range of predetermined wavelengths, based on the input depth.

For example, radiation therapy may involve a percent depth dose, which accounts for the fact that different amounts of radiation may reach different tissue depths, and this depth-dependent variance can depend on the energy spectrum chosen for the radiation. In particular embodiments, hyperthermia techniques disclosed herein may use a depth-dependent dose measurement to precisely deliver hyperthermia to a patient's skin. For example, if a cancer is 3 mm in depth, then hyperthermia may be performed to the entire cancer depth of 0-3 mm, e.g., reaching tissue temperatures of at least 106 to 110 F for the entire depth for the predetermined time period. To achieve this, an infrared hyperthermia heating device may select (or an operator of the device may select) a wavelength for infrared radiation based on the distance of the device to the patient's skin and on the depth of the tissue to be heated. For instance, in the example above, a wavelength may be selected that heats tissue at up to 3 mm relatively efficiently, rather than concentrating absorbed energy in, e.g., the first 1 mm of tissue. In contrast, if a cancer is entirely on the surface, then the infrared hyperthermia heating device may select a wavelength that heats the first 1 mm of tissue but has relatively inefficient heating at greater depths.

To heat a patient's skin, a power density of about 50-100 mW/cm$^2$ at the patient's skin may be used. Therefore, the infrared hyperthermia heating device may be designed so as to emit energy in the selected IR wavelength so that this power density is achieved when the emitter (e.g., emitter 310 of the example implementation of FIG. 3) is positioned at the predetermined distance (e.g., 6-12 inches away) from the patient's skin, whether a handheld infrared hyperthermia heating device or a relatively fixed infrared hyperthermia heating device is used.

Figure 3:
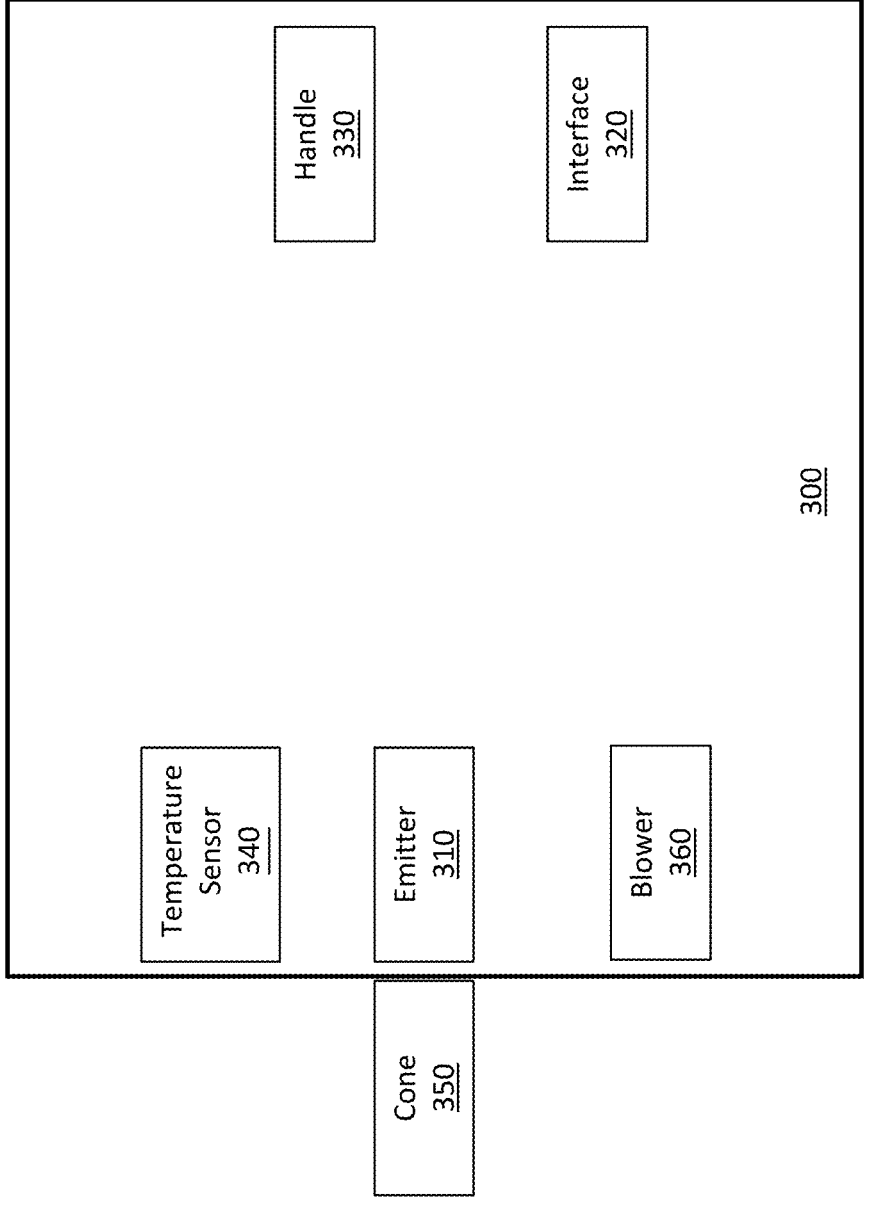
FIG. 3 illustrates an example implementation of an infrared hyperthermia heating device.

In particular embodiments, an infrared hyperthermia heating device may include one more temperature sensors (e.g., one or more temperature sensors 340 of the example implementation of FIG. 3), such as a thermocouple or infrared temperature sensor, to monitor the temperature of the patient's skin. The detected temperature may be output to an operator of the device, for example on a display of the device or of a connected device. In particular embodiments, the detected temperature of a patient's skin may be used as a feedback loop for the hyperthermia procedure. For example, if the detected temperature is too low, or is not rising quickly enough, then the operator of the device may be notified, and may be instructed to move the device closer to the patient's skin and/or to adjust the power output by the device, if the power is variable. As another example, in embodiments in which the infrared hyperthermia heating device is not handheld but is fixed into another piece of equipment, then the position and/or power output of the infrared hyperthermia heating device may be adjusted based on the detected temperature (or based on the rate of change of the detected temperature) of the patient's skin. In particular embodiments, the power output by an infrared hyperthermia heating device may be automatically adjusted based on the temperature of the skin detected by the temperature sensor and/or on a directed distance between the patient's skin and the infrared emitter, for example to consistently maintain the temperature at the predetermined temperature discussed above or to maintain a constant radiation intensity. For example, before the predetermined temperature is reached the infrared hyperthermia heating device may detect the distance between the device and the patient's skin and control the output radiation so as to provide relatively constant intensity from the device. After the predetermined temperature is reached, the device may use detected temperature to control the output radiation intensity (and any temperature modulation, such as a blower) to maintain the patient's skin at the predetermined temperature.

In particular embodiments, the infrared hyperthermia heating device may include a blower (e.g., blower 360 of the example implementation of FIG. 3) that blows ambient air onto the patient's skin while infrared radiation is being supplied, thereby modulating the temperature of the patient's skin. In particular embodiments, a blower may be engaged throughout the heating process, for example to ensure that overheating of the patient's skin does not occur. In other embodiments, the blower may be selectively engaged, for example by the device operator or automatically, e.g., based on the output of a temperature sensor. For example, if a temperature sensor detects that the temperature of a patient's skin exceeds the upper limit of the predetermined temperature, then the infrared hyperthermia heating device may automatically activate the blower mechanism to prevent overheating. This activation may be in conjunction with other temperature modulation techniques, such as reducing the IR energy emitted by the infrared hyperthermia heating device and/or by altering the distance between the device and the patient's skin. In particular embodiments, an infrared hyperthermia heating device may include a variable blower, in that the amount of airflow output by the device is adjustable.

In particular embodiments, an infrared hyperthermia heating device may include a reflector or concentrator to focus infrared radiation on the target area of the patient's skin. In particular embodiments, an infrared hyperthermia heating device may include one or more attachments at the emitter that shape the emitted infrared beam. For example, cancer radiation treatments may use "cones" (e.g., cone 350 of the example implementation of FIG. 3) of various shapes and sizes to match the radiated beam to the area of the cancer. The infrared hyperthermia heating device may include similarly shaped attachments so that the hyperthermia of the patient's skin is matched to the radiated portion of the patient's skin, increasing the effectiveness of the combined radiation-hyperthermia treatment and decreasing unnecessary heating of portions of the patient's skin that did not receive radiation treatment. In particular embodiments, such cones may be removable engaged with the infrared hyperthermia heating device, so that an operator can attach the appropriate cone piece to the infrared hyperthermia heating device.

In particular embodiments, an infrared hyperthermia heating device may automatically record the hyperthermia treatment, including details of the treatment, for inclusion in the patient's medical record. For example, during a treatment session an infrared hyperthermia heating device may record its activation duration, temperature-related information (such as the temperature of the patient's skin as a function of time, the maximum temperature reached, the duration at which the patient's skin was maintained at the predetermined temperature, etc.), the date and time of treatment, settings such as the emissive power and wavelength used, and so. This information may be stored in the device for retrieval by a medical professional, or may be automatically transmitted to a connected device, for example to automatically update a patient's records to reflect the hyperthermia treatment and the corresponding treatment details.

Figure 2:
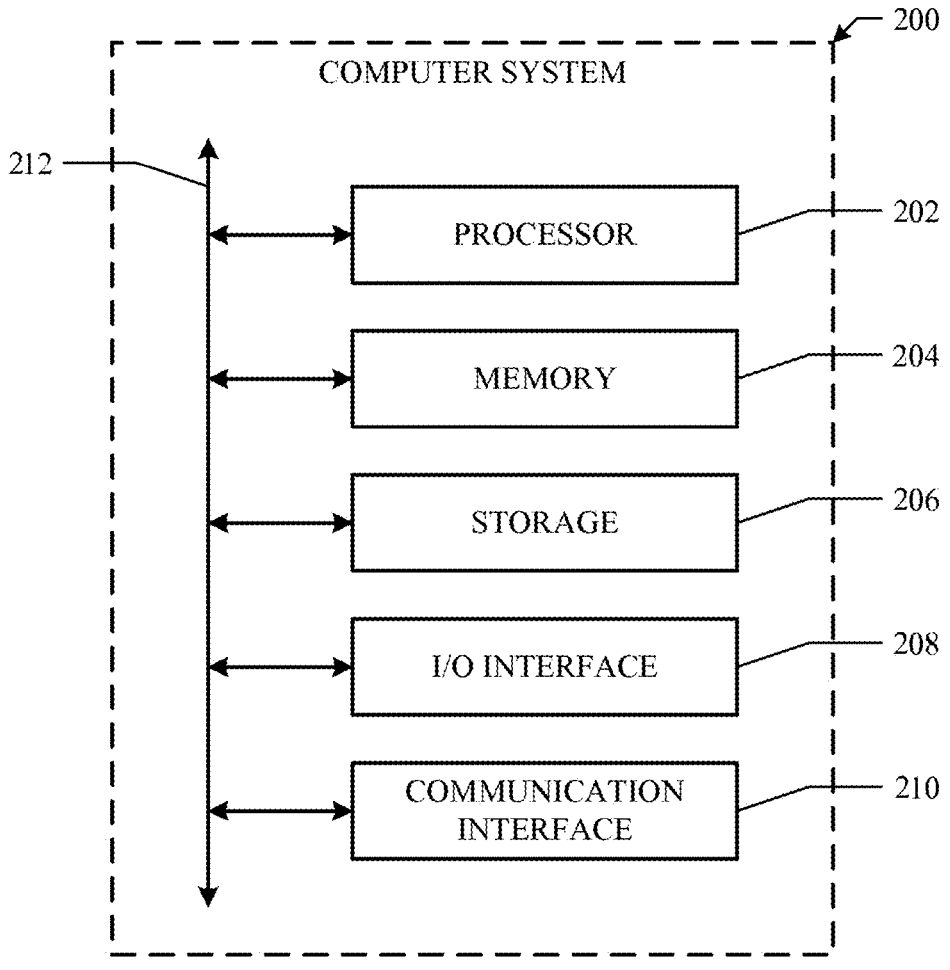
FIG. 2 illustrates an example computing system.

FIG. 2 illustrates an example computer system 200. In particular embodiments, one or more computer systems 200 perform one or more steps of one or more methods described or illustrated herein. In particular embodiments, one or more computer systems 200 provide functionality described or illustrated herein. In particular embodiments, software running on one or more computer systems 200 performs one or more steps of one or more methods described or illustrated herein or provides functionality described or illustrated herein. Particular embodiments include one or more portions of one or more computer systems 200. Herein, reference to a computer system may encompass a computing device, and vice versa, where appropriate. Moreover, reference to a computer system may encompass one or more computer systems, where appropriate.

This disclosure contemplates any suitable number of computer systems 200. This disclosure contemplates computer system 200 taking any suitable physical form. As example and not by way of limitation, computer system 200 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, or a combination of two or more of these. Where appropriate, computer system 200 may include one or more computer systems 200; be unitary or distributed; span multiple locations; span multiple machines; span multiple data centers; or reside in a cloud, which may include one or more cloud components in one or more networks. Where appropriate, one or more computer systems 200 may perform without substantial spatial or temporal limitation one or more steps of one or more methods described or illustrated herein. As an example and not by way of limitation, one or more computer systems 200 may perform in real time or in batch mode one or more steps of one or more methods described or illustrated herein. One or more computer systems 200 may perform at different times or at different locations one or more steps of one or more methods described or illustrated herein, where appropriate.

In particular embodiments, computer system 200 includes a processor 202, memory 204, storage 206, an input/output (I/O) interface 208, a communication interface 210, and a bus 212. Although this disclosure describes and illustrates a particular computer system having a particular number of particular components in a particular arrangement, this disclosure contemplates any suitable computer system having any suitable number of any suitable components in any suitable arrangement.

In particular embodiments, processor 202 includes hardware for executing instructions, such as those making up a computer program. As an example and not by way of limitation, to execute instructions, processor 202 may retrieve (or fetch) the instructions from an internal register, an internal cache, memory 204, or storage 206; decode and execute them; and then write one or more results to an internal register, an internal cache, memory 204, or storage 206. In particular embodiments, processor 202 may include one or more internal caches for data, instructions, or addresses. This disclosure contemplates processor 202 including any suitable number of any suitable internal caches, where appropriate. As an example and not by way of limitation, processor 202 may include one or more instruction caches, one or more data caches, and one or more translation lookaside buffers (TLBs). Instructions in the instruction caches may be copies of instructions in memory 204 or storage 206, and the instruction caches may speed up retrieval of those instructions by processor 202. Data in the data caches may be copies of data in memory 204 or storage 206 for instructions executing at processor 202 to operate on; the results of previous instructions executed at processor 202 for access by subsequent instructions executing at processor 202 or for writing to memory 204 or storage 206; or other suitable data. The data caches may speed up read or write operations by processor 202. The TLBs may speed up virtual-address translation for processor 202. In particular embodiments, processor 202 may include one or more internal registers for data, instructions, or addresses. This disclosure contemplates processor 202 including any suitable number of any suitable internal registers, where appropriate. Where appropriate, processor 202 may include one or more arithmetic logic units (ALUs); be a multi-core processor; or include one or more processors 202. Although this disclosure describes and illustrates a particular processor, this disclosure contemplates any suitable processor.

In particular embodiments, memory 204 includes main memory for storing instructions for processor 202 to execute or data for processor 202 to operate on. As an example and not by way of limitation, computer system 200 may load instructions from storage 206 or another source (such as, for example, another computer system 200) to memory 204. Processor 202 may then load the instructions from memory 204 to an internal register or internal cache. To execute the instructions, processor 202 may retrieve the instructions from the internal register or internal cache and decode them. During or after execution of the instructions, processor 202 may write one or more results (which may be intermediate or final results) to the internal register or internal cache. Processor 202 may then write one or more of those results to memory 204. In particular embodiments, processor 202 executes only instructions in one or more internal registers or internal caches or in memory 204 (as opposed to storage 206 or elsewhere) and operates only on data in one or more internal registers or internal caches or in memory 204 (as opposed to storage 206 or elsewhere). One or more memory buses (which may each include an address bus and a data bus) may couple processor 202 to memory 204. Bus 212 may include one or more memory buses, as described below. In particular embodiments, one or more memory management units (MMUs) reside between processor 202 and memory 204 and facilitate accesses to memory 204 requested by processor 202. In particular embodiments, memory 204 includes random access memory (RAM). This RAM may be volatile memory, where appropriate Where appropriate, this RAM may be dynamic RAM (DRAM) or static RAM (SRAM). Moreover, where appropriate, this RAM may be single-ported or multi-ported RAM. This disclosure contemplates any suitable RAM. Memory 204 may include one or more memories 204, where appropriate. Although this disclosure describes and illustrates particular memory, this disclosure contemplates any suitable memory.

In particular embodiments, storage 206 includes mass storage for data or instructions. As an example and not by way of limitation, storage 206 may include a hard disk drive (HDD), a floppy disk drive, flash memory, an optical disc, a magneto-optical disc, magnetic tape, or a Universal Serial Bus (USB) drive or a combination of two or more of these. Storage 206 may include removable or non-removable (or fixed) media, where appropriate. Storage 206 may be internal or external to computer system 200, where appropriate. In particular embodiments, storage 206 is non-volatile, solid-state memory. In particular embodiments, storage 206 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 206 taking any suitable physical form. Storage 206 may include one or more storage control units facilitating communication between processor 202 and storage 206, where appropriate. Where appropriate, storage 206 may include one or more storages 206. Although this disclosure describes and illustrates particular storage, this disclosure contemplates any suitable storage.

In particular embodiments, I/O interface 208 includes hardware, software, or both, providing one or more interfaces for communication between computer system 200 and one or more I/O devices. Computer system 200 may include one or more of these I/O devices, where appropriate. One or more of these I/O devices may enable communication between a person and computer system 200. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 208 for them. Where appropriate, I/O interface 208 may include one or more device or software drivers enabling processor 202 to drive one or more of these I/O devices. I/O interface 208 may include one or more I/O interfaces 208, where appropriate. Although this disclosure describes and illustrates a particular I/O interface, this disclosure contemplates any suitable I/O interface.

In particular embodiments, communication interface 210 includes hardware, software, or both providing one or more interfaces for communication (such as, for example, packet-based communication) between computer system 200 and one or more other computer systems 200 or one or more networks. As an example and not by way of limitation, communication interface 210 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 210 for it. As an example and not by way of limitation, computer system 200 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 200 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 200 may include any suitable communication interface 210 for any of these networks, where appropriate. Communication interface 210 may include one or more communication interfaces 210, where appropriate. Although this disclosure describes and illustrates a particular communication interface, this disclosure contemplates any suitable communication interface.

In particular embodiments, bus 212 includes hardware, software, or both coupling components of computer system 200 to each other. As an example and not by way of limitation, bus 212 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 212 may include one or more buses 212, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend.

What is claimed is:

1. A method comprising:

positioning a handheld infrared hyperthermia heating device at least a predetermined distance comprising three inches away from an area of a patient's skin treated with radiation therapy;

activating the infrared hyperthermia heating device to heat the area of the patient's skin;

monitoring, by the infrared hyperthermia heating device, a temperature of the area of the patient's skin after activating the infrared hyperthermia heating device, without contacting the patient's skin and while the infrared hyperthermia heating device is positioned at least the predetermined distance;

heating, by the infrared hyperthermia heating device, the area of the patient's skin to a predetermined temperature;

while the monitored temperature of the area of the patient's skin is below the predetermined temperature, then:

detecting a distance between the area of the patient's skin and the infrared hyperthermia heating device; and adjusting, based on the detected distance, an intensity of infrared radiation emitted by the infrared hyperthermia heating device to maintain a constant infrared radiation intensity on the area of the patient's skin;

after the monitored temperature of the area of the patient's skin has reached the predetermined temperature, then varying the intensity of infrared radiation on the area of the patient's skin based on the monitored temperature relative to the predetermined temperature;

maintaining, using the infrared hyperthermia heating device, the predetermined temperature for a predetermined treatment period of time that includes only times during which the monitored temperature of the area of the patient's skin is at least the predetermined temperature;

activating a blower of the infrared hyperthermia heating device to modulate the temperature of the area of patient's skin by blowing air on the area of the patient's skin during at least a portion of the treatment period; and deactivating the infrared hyperthermia heating device after the predetermined period of time to cease heating the area of the patient's skin.

2. The method of claim 1, wherein the predetermined temperature comprises 106° F.-110° F.

3. The method of claim 1, wherein the predetermined period of time comprises 30-90 seconds.

4. The method of claim 1, wherein the infrared hyperthermia heating device emits a single wavelength of infrared radiation.

5. The method of claim 4, wherein the single wavelength comprises wavelength in the range of 3-10 microns.

6. The method of claim 5, further comprising selecting the single wavelength at which the infrared hyperthermia heating device emits radiation.

7. The method of claim 6, wherein the infrared hyperthermia heating device automatically selects the single wavelength based on a hyperthermia treatment depth for the patient.

8. The method of claim 1, further comprising displaying the monitored temperature of the area of the patient's skin on a display of the infrared hyperthermia heating device.

9. The method of claim 1, wherein the amount of constant infrared radiation is based on the monitored temperature.

10. The method of claim 1, further comprising activating the blower of the infrared hyperthermia heating device based on the monitored temperature of the patient's skin.

11. The method of claim 1, further comprising shaping a pattern of infrared radiation emitted by the infrared hyperthermia heating device by attaching, to the infrared hyperthermia heating device, a cone defining the shape of infrared radiation reaching the patient's skin.

12. The method of claim 1, wherein (1) the predetermined temperature comprises a temperature range and (2) the predetermined treatment period of time further includes times during which the monitored temperature of the area of the patient's skin is greater than an upper limit of the temperature range.

13. The method of claim 1, wherein the blower is continuously running during the treatment period of time.

14. The method of claim 1, further comprising varying an airflow of the blower based on the monitored temperature of the area of the patient's skin.

15. An infrared hyperthermia heating device comprising:

an infrared emitter configured to emit a beam of infrared radiation from the device;

an interface configured to activate the infrared emitter so as to emit the beam of infrared radiation from the device;

a handle portion configured to be held by a hand of an operator of the infrared hyperthermia heating device;

a temperature sensor configured to monitor, without contacting a patient's skin and while the infrared hyperthermia heating device is positioned at a distance comprising at least a predetermined distance of at least three inches from the patient's skin, a temperature of an area of the patient's skin upon which the beam of infrared radiation is incident after the infrared hyperthermia heating device is activated; and a blower configured to modulate the temperature of the area of patient's skin by blowing air on the area of the patient's skin during at least a portion of a predetermined treatment period of time;

one or more non-transitory computer-readable storage media comprising instructions; and one or more processors coupled to the one or more storage media and configured to execute the instructions to:

maintain, using the emitted beam of infrared radiation, the temperature of the area of the patient's skin at a predetermined temperature for the predetermined treatment period of time that includes only times during which the monitored temperature of the area of the patient's skin is at least the predetermined temperature;

while the monitored temperature of the area of the patient's skin is below the predetermined temperature, then:

detect the distance between the area of the patient's skin and the infrared hyperthermia heating device; and adjust, based on the detected distance, an intensity of infrared radiation emitted by the infrared hyperthermia heating device to maintain a constant infrared radiation intensity on the area of the patient's skin; and after the monitored temperature of the area of the patient's skin has reached the predetermined temperature, then vary the intensity of infrared radiation on the area of the patient's skin based on the monitored temperature relative to the predetermined temperature.

16. The device of claim 15, wherein the one or more processors are further configured to execute the instructions to vary the intensity of infrared radiation on the area of the patient's skin based on the monitored temperature relative to the predetermined temperature by:

comparing the monitored temperature to the predetermined temperature; and adjusting, based on the comparison, the intensity of the beam of infrared radiation emitted from the device.

17. The device of claim 15, wherein the emitted beam of infrared radiation comprises a single infrared wavelength.

18. The device of claim 15, wherein the one or more processors are further configured to execute the instructions to:

select a wavelength of the emitted infrared radiation based on depth of radiation treatment for a patient.

19. The device of claim 15, further comprising a cone configured to removably couple to a body of the device, wherein the cone comprises an opening configured to shape the emitted beam of infrared radiation.

20. The device of claim 15, wherein the predetermined temperature comprises 106° F.-110° F.

21. The device of claim 15, wherein the predetermined treatment period of time comprises 30-90 seconds.

22. The infrared hyperthermia heating device of claim 15, wherein the blower is configured to continuously run during the treatment period of time.

23. The infrared hyperthermia heating device of claim 15, wherein the one or more processors are further configured to execute the instructions to vary an airflow of the blower based on the monitored temperature of the area of the patient's skin.

* * * * *